US006777436B2

(12) United States Patent
Yokoyama et al.

(10) Patent No.: US 6,777,436 B2
(45) Date of Patent: Aug. 17, 2004

(54) INTRAOCULAR TENSION LOWERING COMPOSITIONS FOR TOPICAL ADMINISTRATION

(75) Inventors: Tomihisa Yokoyama, Saitama (JP); Takashi Shiokari, Saitama (JP)

(73) Assignee: Sankyo Company, Limited, Tokyo (JP)

( * ) Notice: Subject to any disclaimer, the term of this patent is extended or adjusted under 35 U.S.C. 154(b) by 39 days.

(21) Appl. No.: 10/016,535

(22) Filed: Dec. 10, 2001

(65) Prior Publication Data

US 2002/0147211 A1 Oct. 10, 2002

Related U.S. Application Data

(63) Continuation-in-part of application No. PCT/JP00/03779, filed on Jun. 9, 2000.

(30) Foreign Application Priority Data

Jun. 11, 1999 (JP) ............................................ 11-164945

(51) Int. Cl.[7] ........................ A61K 31/41; A61K 33/22; A61K 31/198
(52) U.S. Cl. ........................ 514/381; 514/566; 424/660
(58) Field of Search ................................. 514/303, 340, 514/381, 395, 397, 566; 424/660

(56) References Cited

U.S. PATENT DOCUMENTS

| 5,889,020 A | 3/1999 | Huxley et al. | 514/303 |
| 5,925,664 A | 7/1999 | Yokoyama et al. | 514/382 |

FOREIGN PATENT DOCUMENTS

| CN | 1105239 A | 7/1995 |
| EP | 0 631 780 A | 1/1995 |
| EP | 0 795 326 A | 9/1995 |
| JP | 7-324034 A | 12/1995 |
| WO | 91/15206 A | 10/1991 |
| WO | WO 095/01176 A1 | 1/1995 |

Primary Examiner—Phyllis G. Spivack
(74) Attorney, Agent, or Firm—Frishauf, Holtz, Goodman & Chick, P.C.

(57) ABSTRACT

An intraocular tension lowering composition for topical administration is disclosed which comprises an effective amount of an (i) angiotensin II antagonist, (ii) a boric aid and (iii) an ethylenediamine tetraacetic acid. Said composition has excellent intraocular tension lowering activity. Said composition may be effectively administered to humans and other warm-blooded animals to lower intraocular tension.

27 Claims, No Drawings

INTRAOCULAR TENSION LOWERING COMPOSITIONS FOR TOPICAL ADMINISTRATION

This application is a continuation-in-part application of International Application PCT/JP00/03779 filed Jun. 9, 2000 which was not published under PCT Article 21(2) in English.

The present invention relates to a novel medical composition for topical administration showing excellent intraocular tension lowering activity.

BACKGROUND OF THE INVENTION

It has been well known that angiotensin II antagonists lower intraocular tension when topically administered (EP 795326 (and U.S. Pat No. 5,925,664), EP 631780, WO 95/21609, WO 91/15206, etc.). In particular, the following compounds are known as representative drugs.

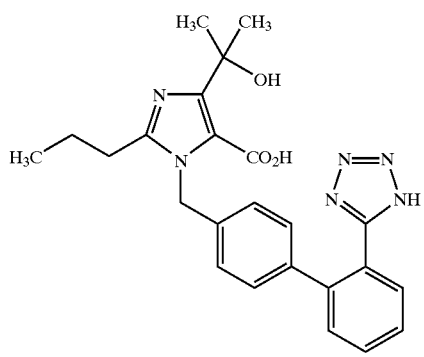

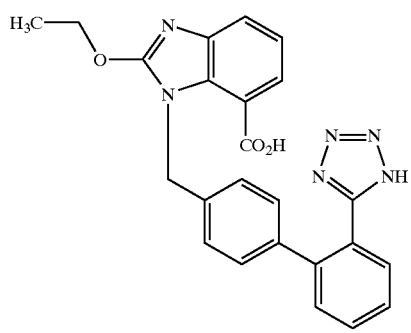

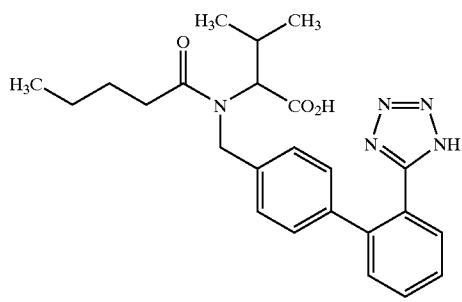

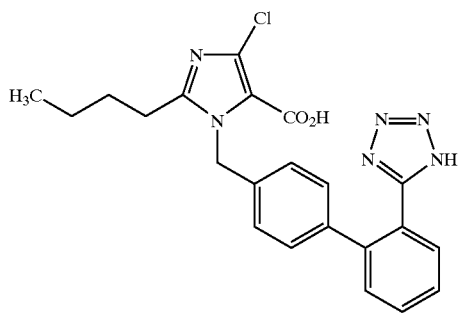

SUMMARY OF THE INVENTION

As the result of various investigation on preparations and pharmacologies of topical compositions containing angiotensin II antagonists, the present inventors have found that the intraocular tension lowering activity of angiotensin II antagonists can be reinforced by adding one or more boric acids and one or more ethylenediamine tetraacetic acids to the composition.

The present invention relates to:

(1) an intraocular tension lowering topical composition containing an angiotensin II antagonist, a boric acid and an ethylenediamine tetraacetic acid.

Said composition preferably is (2) a composition in which the angiotensin II antagonist is a compound of the following general formula (I) or a pharmacologically acceptable salt or derivative thereof:

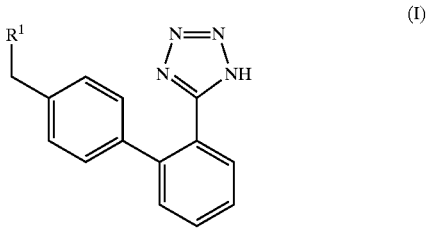

(I)

wherein $R^1$ represents a group of the following structure (Ia), (Ib), (Ic), (Id), (Ie) or (If):

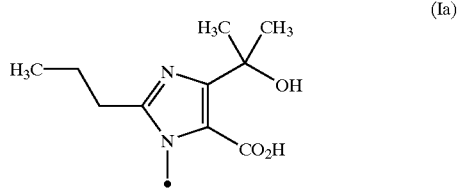

(Ia)

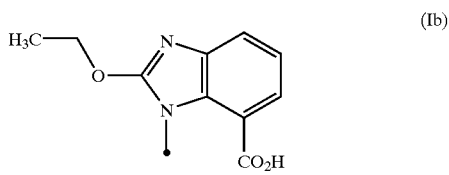

(Ib)

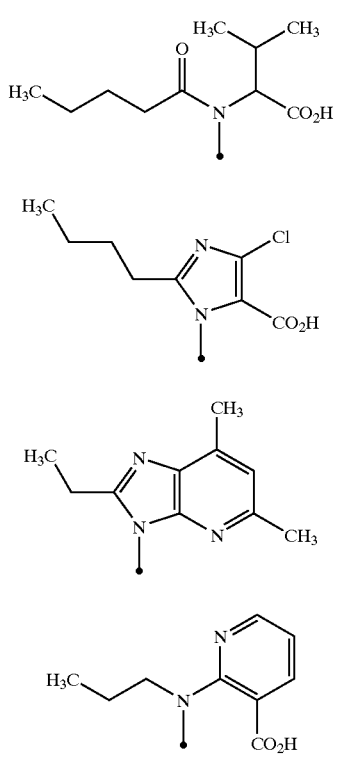

(3) a composition in which $R^1$ represents a group of the structure (Ia), (Ib) or (Ic);

(4) a composition in which the compound of general formula (I) is a compound selected from 4-(1-hydroxy-1-methylethyl)-2-propyl-1-{4-[2-(tetrazol-5-yl) phenyl]phenyl}methylimidazole-5-carboxylic acid and 2-ethoxy-1-[2'-(1H-tetrazol-5-yl) biphenyl-4-yl] methyl-1H-benzimidazole-7-carboxylic acid;

(5) a composition additionally containing a preservative; and (6) a composition in which the preservative is a paraben.

Further, another object of the present invention is to provide a method of lowering intraocular tension which comprises administering a composition as described in any one of (1) to (6) above containing a pharmacologically effective amount of an angiotensin II antagonist to a warm-blooded animal (preferably human). In particular, it is to provide a method of lowering intraocular tension caused by glaucoma (including glaucoma with normal intraocular tension) or ocular hypertension.

In the present invention, "boric acid" includes boric acid and compounds which function equivalent to a boric acid. A substance equivalent to boric acid is a compound that gives rise to borate ion when dissolved in water. Examples of such compounds are boric anhydride ($B_2O_3$), tetraboric acid ($H_2B_4O_7$), as well as pharmacologically acceptable salts of boric acid, boric anhydride, and tetraboric acid. Boric acid, boric anhydride, borax and sodium borate decahydrate are preferred. Boric acid is more preferred.

These boric acids may be used singly or in combination of two or more members.

"Ethylenediamine tetraacetic acid" includes ethylenediamine tetraacetic acid and compounds which function equivalent to ethylenediamine tetraacetic acid. A substance equivalent to ethylenediamine tetraacetic acid is a compound that gives rise to an ethylenediamine tetraacetate ion when dissolved in water. Such compounds include pharmacologically acceptable salts of ethylenediamine tetraacetic acid, and appropriate examples thereof are ethylenediamine tetraacetic acid, disodium ethylenediamine tetraacetate dihydrate, trisodium ethylenediamine tetraacetate trihydrate, disodium ethylenediamine tetraacetate dihydrate, and tetrasodium ethylenediamine tetraacetate tetrahydrate. Disodium ethylenediamine tetraacetate dihydrate is most preferred.

These ethylenediamine tetraacetic acids may be used singly or in combination of two or more members.

"Angiotensin II antagonists" preferably mean the compounds of the following general formula (I) or pharmacologically acceptable salts or derivatives thereof:

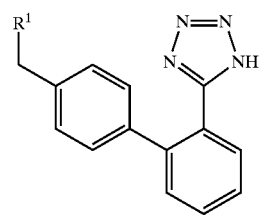

(I)

wherein $R^1$ represents a group of the following structures (Ia), (Ib), (Ic), (Id), (Ie) or (If):

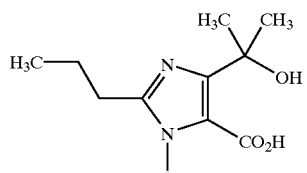

(Ia)

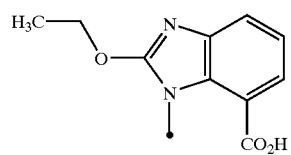

(Ib)

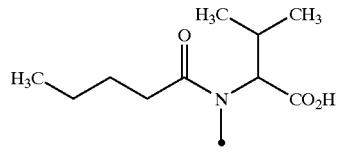

(Ic)

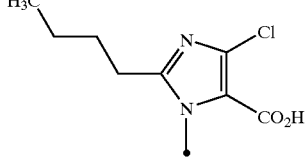

(Id)

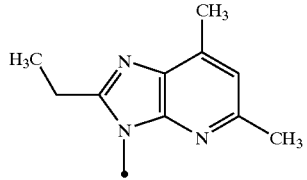

(Ie)

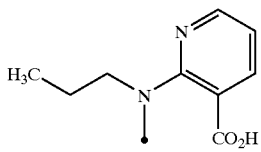

(If)

More preferably, the compound is 4-(1-hydroxy-1-methylethyl)-2-propyl-1-{4-[2-(tetrazol-5-yl)phenyl]phenyl}methylimidazole-5-carboxylic acid and 2-ethoxy-1-[2'-(1H-tetrazol-5-yl)biphenyl-4-yl]methyl-1H-benzimidazole-7-carboxylic acid, or a pharmacologically acceptable salt or derivative thereof.

"Pharmacologically acceptable salts" mean those salts that may be prepared by reacting the compound of general formula (I) above, boric acids, or ethylenediamine tetraacetic acids with a base. Examples of such salts include metal salts including alkali metal salts such as sodium salts, potassium salts, lithium salts, etc., alkaline earth metal salts such as calcium salts, magnesium salts, etc., aluminium salts and ferrous salts, etc.; amine salts including inorganic salts such as ammonium salts, etc., organic salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethylammonium salts, tris(hydroxymethyl)aminomethane salts, etc.; and amino acid salts such as glycine salts, lysine salts, arginine salts, ornithine salts, glutamic acid salts, aspartic acid salts, etc. Of them, alkali metal salts are preferred, and sodium salts and potassium salts are more preferred.

Boric acids, ethylenediamine tetraacetic acids, and the compounds of the general formula (I) above or their pharmacologically acceptable salts may occasionally absorb water so that the absorbed water is incorporated, ie they become a hydrate, by allowing them to stand in the air or during recrystallization. Such hydrates are included in the present invention.

When the compound (i) has hydroxyl groups and/or carboxyl groups, such a compound can be converted into its derivatives by modifying those groups. So, pharmaceutically acceptable derivatives of the compound of the general formula (I) above mean such derivatives. Such derivatives include "esters of hydroxyl groups", "ethers of hydroxyl groups", "esters of carboxyl groups" and "amides of carboxyl groups" and the residues of such ester, ether or amide groups include "general protecting groups" or "protecting groups capable of being cleaved by biological means like hydrolysis within living bodies".

"General protecting groups" mean protecting groups capable of being cleaved by chemical methods such as hydrogenation, hydrolysis, electrolysis, photolysis, etc.

"General protecting groups" comprising the residue of "esters of hydroxyl groups" and "ethers of hydroxyl groups" preferably mean aliphatic acyl groups (preferably lower aliphatic acyl groups having 1 to 6 carbon atoms) including alkanoyl groups such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl, heneicosanoyl, etc., halogeno-alkylcarbonyl groups such as chloroacetyl, dichloroacetyl, trichloroacetyl, trifluoroacetyl, etc., lower alkoxyalkylcarbonyl groups such as methoxyacetyl, etc., unsaturated alkylcarbonyl groups such as acryloyl, propioloyl, methacryloyl, crotonoyl, isocrotonoyl, (E)-2-methyl-2-butenoyl etc.; aromatic acyl groups including arylcarbonyl groups such as benzoyl, α-naphthoyl, β-naphthoyl, etc., halogenoarylcarbonyl groups such as 2-bromobenzoyl, 4-chlorobenzoyl, etc., lower alkylarylcarbonyl groups such as 2,4,6-trimethylbenzoyl, 4-toluoyl, etc., lower alkoxyarylcarbonyl groups such as 4-anisoyl, etc., nitroarylcarbonyl groups such as 4-nitrobenzoyl, 2-nitrobenzoyl, etc., lower alkoxycarbonylarylcarbonyl groups such as 2-(methoxycarbonyl)benzoyl, etc. and arylarylcarbonyl groups such as 4-phenylbenzoyl, etc.; alkoxycarbonyl groups including lower alkoxycarbonyl groups such as methoxycarbonyl, ethoxycarbonyl, propoxycarbonyl, butoxycarbonyl, s-butoxycarbonyl, t-butoxycarbonyl, isobutoxycarbonyl, etc., lower alkoxycarbonyl groups substituted with halogen atoms or tri-lower alkylsilyl groups such as 2,2,2-trichloroethoxycarbonyl, 2-trimethylsilylethoxycarbonyl, etc; tetrahydropyranyl or tetrahydrothiopyranyl groups such as tetrahydropyran-2-yl, 3-bromotetrahydropyran-2-yl, 4-methoxytetrahydropyran-4-yl, tetrahydrothiopyran-2-yl-4-methoxytetrahydrothiopyran-4-yl, etc.; tetrahydrofuranyl or tetrahydrothiofuranyl groups such as tetrahydrofuran-2-yl, tetrahydrothiofuran-2-yl, etc.; silyl groups including tri-lower alkylsilyl groups such as trimethylsilyl, triethylsilyl, isopropyldimethylsilyl, t-butyldimethylsilyl, methyldiisopropylsilyl, methyldi-t-butylsilyl, triisopropylsilyl, etc., tri-lower alkylsilyl groups where 1 or 2 of the alkyl groups are replaced by 1 or 2 aryl groups such as diphenylmethylsilyl, diphenylbutylsilyl, diphenylisopropylsilyl, phenyldiisopropylsilyl, etc; alkoxymethyl groups including lower alkoxymethyl groups such as methoxymethyl, 1,1-dimethyl-1-methoxymethyl, ethoxymethyl, propoxymethyl, isopropoxymethyl, butoxymethyl, t-butoxymethyl, etc., lower alkoxy-lower alkoxymethyl groups such as 2-methoxyethoxymethyl, etc., halogeno lower alkoxymethyl groups such as 2,2,2-trichloroethoxymethyl, bis(2-chloroethoxy)methyl, etc.; substituted ethyl groups including lower alkoxyethyl groups such as 1-ethoxyethyl, 1-(isopropoxy)ethyl, etc., halogenoethyl groups such as 2,2,2-trichloroethyl, etc.; aralkyl groups including lower alkyl groups (such as $C_1$-$C_6$ straight or branched chain alkyl, preferably methyl, ethyl, propyl, isopropyl or butyl, and more preferably methyl or ethyl), substituted with 1 to 3 aryl groups such as benzyl, α-naphthylmethyl, β-naphthylmethyl, diphenylmethyl, triphenylmethyl, α-naphthyldiphenylmethyl, 9-anthrylmethyl, etc., lower alkyl groups substituted with 1 to 3 aryl groups where said aryl group is substituted with one or more lower alkyl, lower alkoxy (such as $C_1$-$C_4$ straight or branched chain alkoxy, preferably methoxy, ethoxy, propoxy, isopropoxy or butoxy, and more preferably methoxy or ethoxy), nitro, halogen or cyano groups, e.g. 4-methylbenzyl, 2,4,6-trimethylbenzyl, 3,4,5-trimethylbenzyl, 4-methoxybenzyl, 4-methoxyphenyidiphenylmethyl, 2-nitrobenzyl, 4-nitrobenzyl, 4-chlorobenzyl, 4-bromobenzyl, 4-cyanobenzyl, etc.; alkenyloxycarbonyl groups such as vinyloxycarbonyl, allyloxycarbonyl, etc.; and aralkyloxycarbonyl groups where said aryl group may be substituted with 1 or 2 lower alkoxy or nitro groups, e.g. benzyloxycarbonyl, 4-methoxybenzyloxycarbonyl, 3,4-dimethoxybenzyloxycarbonyl, 2-nitrobenzyloxycarbonyl, 4-nitrobenzyloxycarbonyl, etc.

"General protecting groups" comprising the residue of "esters of carboxyl groups" preferably mean lower alkyl groups such as methyl, ethyl, propyl, isopropyl, n-butyl, isobutyl, s-butyl, tert-butyl, n-pentyl, isopentyl, 2-methylbutyl, neopentyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimetlhylbutyl, 1,3-dimethylbutyl, 2,3-dimethylbutyl, 2-ethylbutyl, etc.; lower alkenyl groups such as vinyl, 2-propenyl, 1-methyl-2-propenyl, 2-methyl-2-propenyl, 2-ethyl-2-propenyl, 2-butenyl, 1-methyl-2-butenyl, 2-methyl-2-butenyl, 1-ethyl-2-butenyl, 3-butenyl, 1-methyl-3-butenyl, 2-methyl-3-butenyl, 1-ethyl-3-butenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl4-pentenyl, 2-methyl4-pentenyl, 2-hexenyl, 3-hexenyl, 4-hexenyl, 5-hexenyl, etc.; lower alkynyl groups such as ethynyl, 2-propynyl, 1-methyl-2-propynyl, 2-butynyl, 1-methyl-2-butynyl, 1-ethyl-2-butynyl, 3-butynyl, 1-methyl-3-butynyl, 2-methyl-3-butynyl, 1 ethyl-3-butynyl 2pentynyl, 1methyl 2-pentynl-3-pentynyl, 4-pentynyl 2-hexynyl, 3-hexynyl, 4-hexynyl, 5-hexynyl, etc.; halogeno lower alkyl groups such as trifluoromethyl, trichloromethyl, difluoromethyl, dichloromethyl, dibromomethyl, fluoromethyl, 2,2,2-trichloroethyl, 2,2,2-trifluoroethyl, 2-bromoethyl, 2-chloroethyl, 2-fluoroethyl, 2,2-dibromoethyl, etc.; hydroxy lower alkyl groups such as 2-hydroxyethyl, 2,3-dihydroxypropyl, 3-hydroxypropyl, 3,4-dihyidroxybutyl, 4-hydroxybutyl, etc.; lower aliphatic acyl - lower alkyl groups such as acetylmethyl, etc.; aralkyl groups mentioned above; and silyl groups mentioned above.

"Protecting groups capable of being cleaved by biological means like hydrolysis within living bodies" mean protecting groups which can be cleaved by hydrolysis or the like within living bodies to yield the original compound or its pharmacologically acceptable salt. Whether a group is a "protecting group capable of being cleaved by biological means like hydrolysis within living bodies" or not can be determined by administering such a derivative by intravenous injection into test animals such as rats or mice, examining the body liquid thereafter and detecting the original compound or its pharmacologically acceptable salt.

"Protecting groups capable of being cleaved by biological means like hydrolysis within living bodies" comprising the residue of "esters of hydroxyl groups" and "ethers of hydroxyl groups" preferably mean carbonyloxyalkyl groups, for example, 1-(acyloxy)lower alkyl groups including 1-(lower aliphatic acyloxy)-lower alkyl groups such as formyloxymethyl, acetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl, 1-pivaloyloxyhexyl, etc., 1-(cycloalkyl-carbonyloxy)-lower alkyl groups such as cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl, 1-cyclohexylcarbonyloxybutyl, etc., 1-(aromatic acyloxy)-lower alkyl groups such as benzoyloxymethyl, etc.; lower alkoxycarbonyloxy)alkyl groups such as methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, cyclohexyloxycarbonyloxymethyl, cyclohexyloxycarbonyloxy(cyclohexyl)methyl, 1-(methoxycarbonyloxy)ethyl, 1-(ethoxycarbonyloxy)ethyl, 1-(propoxycarbonyloxy)ethyl, 1-(isopropoxycarbonyloxy)ethyl, 1-(butoxycarbonyloxy)ethyl, 1-(isobutoxycarbonyloxy)ethyl, 1-(t-butoxycarbonyloxy)ethyl, 1-(pentyloxycarbonyloxy)ethyl, 1-(hexyloxycarbonyloxy)ethyl, 1-(cyclopentyloxycarbonyloxy)ethyl, 1-(cyclopentyloxycarbonyloxy)propyl, 1-(cyclohexyloxycarbonyloxy)propyl, 1-(cyclopentyloxycarbonyloxy)butyl, 1-(cyclohexyloxycarbonyloxy)butyl, 1-(cyclohexyloxycarbonyloxy)ethyl, 1-(ethoxycarbonyloxy)propyl, 1-(methoxycarbonyloxy)propyl, 1-(ethoxycarbonyloxy)propyl, 1-(propoxycarbonyloxy)propyl, 1-(isopropoxycarbonyloxy)propyl, 1-(butoxycarbonyloxy)propyl, 1-(isobutoxycarbonyloxy)propyl, 1-(pentyloxycarbonyloxy)propyl, 1-(hexyloxycarbonyloxy)propyl, 1-(methoxycarbonyloxy)butyl, 1-(ethoxycarbonyloxy)butyl, 1-(propoxycarbonyloxy)butyl, 1-(isopropoxycarbonyloxy)butyl, 1-(butoxycarbonyloxy)butyl, 1-(isobutoxycarbonyloxy)butyl, 1-(methoxycarbonyloxy)pentyl, 1-(ethoxycarbonyloxy)pentyl, 1-(methoxycarbonyloxy)hexyl, 1-(ethoxycarbonyloxy)hexyl, etc.; oxodioxolenylmethyl groups such as (5-phenyl-2-oxo-1,3-dioxolen4-yl)methyl, [5-(4-methylphenyl)-2-oxo-1,3-dioxolen4-yl]methyl, [5-(4-methoxyphenyl)-2-oxo-1,3-dioxolen4-yl]methyl, [5-(4-fluorophenyl)-2-oxo-1,3-dioxolen4-yl]methyl, [5-(4-chlorophenyl)-2-oxo-1,3-dioxolen4-yl]methyl, (2-oxo-1,3-dioxolen4-yl)methyl, (5-methyl-2-oxo-1,3-dioxolen4-yl)methyl, (5-ethyl-2-oxo-1,3-dioxolen4-yl)methyl, (5-propyl-2-oxo-1,3-dioxolen4-yl)methyl, (5-isopropyl-2-oxo-1,3-dioxolen4-yl)methyl, (5-butyl-2-oxo-1,3-dioxolen4-yl)methyl, etc.; phthalidyl groups such as phthalidyl, dimethylphthalidyl, dimethoxyphthalidyl, etc.; lower aliphatic acyl groups mentioned above; aromatic acyl groups mentioned above; residues of a succinic acid half ester salt; residues of a phosphoric acid ester salt; residues of ester-forming groups such as amino acids; carbamoyl groups; carbamoyl groups substituted with 1 or 2 lower alkyl groups; and 1-(acyloxy)alkyloxycarbonyl groups such as pivaloyloxymethyloxycarbonyl, etc. Carbonyloxyalkyl groups are preferred.

On the other hand, "protecting groups capable of being cleaved by biological means like hydrolysis within living bodies" comprising the residue of "esters of carboxy groups" preferably mean alkoxy-lower alkyl groups including lower alkoxy-lower alkyl groups such as methoxyethyl, 1-ethoxyethyl, 1-methyl-1-methoxyethyl, 1-(isopropoxy)ethyl, 2-methoxyethyl, 2-ethoxyethyl, 1,1-dimethyl-1- methoxyethyl, ethoxymethyl, n-propoxymethyl, isopropoxymethyl, n-butoxymethyl, t-butoxymethyl, etc., lower alkoxy-lower alkyl groups such as 2-methoxyethoxymethyl, etc., aryloxy-lower alkyl groups such as phenoxymethyl, etc., (halogeno lower alkoxy)-lower alkyl groups such as 2,2,2-trichloroethoxymethyl, bis(2-chloroethoxy)methyl, etc.; (lower alkoxy-carbonyl)lower alkyl groups such as methoxycarbonylmethyl, etc,; cyano-lower alkyl groups such as cyanomethyl, 2-cyanoethyl, etc.; (lower alkyl)thiomethyl groups such as methylthiomethyl, ethylthiomethyl, etc.; arylthiomethyl groups such as phenylthiomethyl, naphthylthiomethyl, etc.; (optionally halogenated lower alkyl)-sulfonyl lower alkyl groups such as 2-methanesulfonylethyl, 2-trifluoromethanesulfonylethyl, etc.; (aryl sulfonyl)-lower alkyl groups such as 2-benzenesulfonylethyl, 2-tolenesulfonylethyl, etc.; 1-(acyloxy)-lower alkyl groups mentioned above; phthalidyl groups mentioned above; lower alkyl groups mentioned above; carboxyalkyl groups such as carboxymethyl, etc.; and residues of amide-forming groups of amino acids" such as phenylalanine, etc.

The intraocular tension lowering composition for topical administration of the present invention can be prepared in a conventional manner by using one or more angiotensin II antagonists, one or more boric acids and one or more ethylenediamine tetraacetic acids. For example, the ophthalmic composition can be used in a formulation suitable for topical administration such as eye drops e.g. aqueous eye drops, aqueous ophthalmic suspensions, non-aqueous eye drops and non-aqueous ophthalmic suspensions, gels, ophthalmic ointments, etc. For preparing such formulations, pharmacologically acceptable carriers may be added to said ingredients. No limitation is given to the carriers to be used if they are those customarily applied to ophthalmic formulations, and they illustratively include inert diluents, preservatives, isotonic agents, buffering agents, pH regulating agents, thickeners, surfactants, ointment bases, and the like.

Examples of inert diluents include aqueous solvents such as water, Ringer solution, isotonic saline, etc. or oily solvents such as castor oil, olive oil, sesame oil, soybean oil, liquid paraffin, propylene glycol, β-octyldodecanol, etc.

Examples of preservatives include parabens such as methylparaben, ethylparaben, propylparaben, butylparaben, etc., benzalkonium chloride, chlorohexidine, benzethonium chloride, benzyl alcohol, sorbic acid and its salts, thimerosal, chlorobutanol, etc. Parabens, benzalkonium chloride and benzethonium chloride are preferred.

Since excellent preservative effects can be attained by using boric acids and ethylenediamine tetraacetic acids together with parabens, the parabens are most preferred.

Examples of isotonic agents are sodium chloride, mannitol, sorbitol, glycerin, etc.

Examples of buffering agents are phosphates, acetates, citrates, etc.

Examples of pH regulating agents are hydrochloric acid, acetic acid, sodium hydroxide, and the like.

Examples of ointment bases are vaseline, plastibase (trade mark), liquid paraffin, etc.

Examples of thickeners are methyl cellulose, carmelose and its salts, hydroxyethyl cellulose, sodium alginate, carboxy vinyl polymer, polyvinylpyrrolidone, and the like.

Examples of surfactants are polyethylene glycol, polypropylene glycol, polyoxyethylene hardened castor oil, polysorbate, etc.

For preparing a gel, for example, carboxyvinyl polymer, methyl cellulose, sodium alginate, hydroxypropyl cellulose, ethylene maleic anhydride polymer and the like can be used.

Concerning the formulation of the topical composition of the present invention, a lower amount of the angiotensin II antagonist is 0.001% (preferably 0.01%) and an upper amount is 10% (preferably 5%).

For the amount of the boric acid compound in the composition, a lower amount is suitably 0.05% (preferably 0.1%, and more preferably 0.5%) and an upper amount is suitably 10% (preferably 5%, and more preferably 2%), calculated as boric acid.

For the amount of the ethylenediamine tetraacetic acid compound in the composition, a lower amount is suitably 0.00025% (preferably 0.0005%, and more preferably 0.005%) and an upper amount is suitably 0.2% (preferably 0.1%, and more preferably 0.05%), calculated as disodium ethylenediamine tetraacetate dihydrate.

The above percents are each a percent by weight (in grams) of the component per 100 ml of the volume of the total pharmacological (ophthalmic) composition, namely w/v %. Thus, "1%" equals 0.01 g/mL which equals 1 g/100 mL.

The relative amounts of the boric acid compound and the ethylenediamine tetraacetic acid compound follow: The lower weight ratio of the amount of the ethylenediamine tetraacetic acid compound (calculated as noted above) relative to the boric acid compound (calculated as noted above) is suitably 0.00025:1 (preferably 0.0005:1 and more preferably 0.005:1); and the upper ratio is suitably 0.2:1 (preferably 0.1:1 and more preferably 0.05:1).

The dose of the composition of the present invention differs, depending upon the patient's (e.g., human) condition. When the composition of the present invention is used as eye drops, for example, one to several drops per unit dose, preferably 1 or 2 drops (about 50 $\mu$L per 1 drop), are applicable about 1 to about 6 times daily. Although the method of the present invention preferably applies the combination of the three active components in the form of a composition, the three active components may also be applied separately but substantially simultaneously to an eye. The references herein to lower intraocular tension refers to lowering of intraocular pressure.

The composition and method of the present invention may be applied to an eye of a warm-blooded animal, and particularly a human.

A concrete description of the present invention will now be illustrated by the following Examples and Experiments, but the scope of the present invention is not limited thereby.

Examples

Example 1

Eye Drops

A hot solution of 6.6 mg of methylparaben and 3.6 mg of propylparaben in 14 ml of water for injection is cooled down to room temperature, and 0.29 of boric acid and 1 mg of disodium ethylenediamine tetraacetate dihydrate were added thereto to give a solution.

To this solution were added 0.1 g of 4-(1-hydroxy-1-methylethyl)-2-propyl-1-{4-[2-(tetrazol-5-yl)phenyl]phenyl}methylimidazole-5-carboxylic acid (hereinafter referred to as "Compound A") and 61 mg of sodium chloride, and then about 0.4 ml of a 1 mol/L aqueous solution of sodium hydroxide was added. The resultant mixture was adjusted to pH 7.0 with an aqueous solution of sodium hydroxide (concentration: 1 mol/L) and diluted with water for injection up to a total volume of 20 ml.

This solution was aseptically filtered through Membrane Filter (Manufactured by MILLIPORE Corp.) [Hydrophilic Durapore (Material: hydrophilic polyvinylidene difluoride), 0.22 μm (hereinafter referred to as "GV")] to give the eye drops formulation.

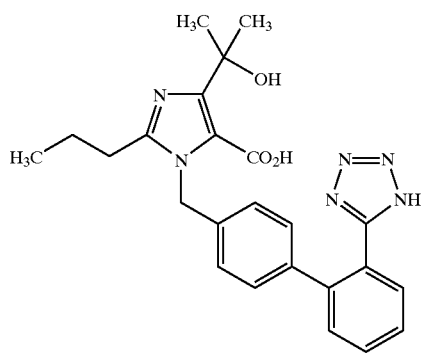

Compound A

Example 2

Eye Drops

Preparation was carried out in the same manner as described in Example 1, except that 2-ethoxy-1-[2'-(1H-tetrazol-5-yl)biphenyl4-yl]methyl-1H-benzimidazole-7-carboxylic acid (hereinafter referred to as "Compound B") was used in place of Compound A, to give the following eye drops formulation.

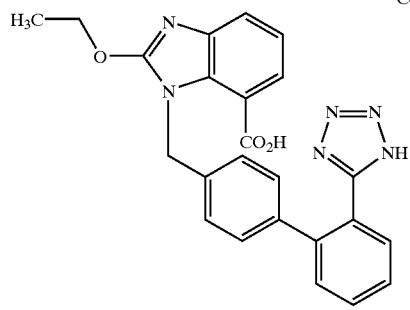

Compound B

Formulation (mg/mL)

| Compound B | 20 |
|---|---|
| Methylparaben | 0.33 |
| Propylparaben | 0.18 |
| Boric acid | 10 |
| EDTA-2Na | 0.05 |

("EDTA-2Na" represents disodium ethylenediamine tetraacetate dihydrate. In addition to the description above, appropriate amounts of sodium hydroxide and hydrochloric acid were added for adjusting to pH 7.0.)

Example 3

Preparation was carried out in the same manner as described in Example 1, except that N-valeryl-N-[(2'-(1H-tetrazol-5-yl)biphenyl-4-yl)methyl]-valine (hereinafter referred to as "Compound C") was used in place of Compound A, to give the following eye drops formulation.

Compound C

Formulation (mg/mL)

| Compound C | 39.1 |
|---|---|
| Methylparaben | 0.33 |
| Propylparaben | 0.18 |
| Boric acid | 10 |
| EDTA-2Na | 0.05 |
| Sodium chloride | 2.80 |

("EDTA-2Na" represents disodium ethylenediamine tetraacetate dihydrate. In addition to the description above, appropriate amounts of sodium hydroxide and hydrochloric acid were added for adjusting to pH 7.0.)

Comparative Examples

For evaluating the topical composition of the present invention, the following compositions were prepared, and compared with the composition of the Examples above in experiments described below.

Comparative Example 1

In 14 ml of water for injection were dissolved with heating 6.6 mg of methylparaben and 3.6 mg of propylparaben.

To this solution were added 0.1 g of Compound A and 166.2 mg of sodium chloride, and then about 0.4 ml of a 1 mol/L aqueous solution of sodium hydroxide was added and dissolved with stirring. This solution was adjusted to pH 7.0 with an aqueous solution of sodium hydroxide (concentration: 1 mol/L) and diluted with water for injection up to a total volume of 20 ml.

This solution was aseptically filtered with GV to give an eye drops formulation.

Comparative Example 2

In 14 ml of water for injection were dissolved with heating 6.6 mg of methylparaben and 3.6 mg of propylparaben. The resultant solution was cooled down to room temperature and mixed with 1 mg of disodium ethylenediamine tetraacetate dihydrate to give a solution.

To this solution were added 0.1 g of Compound A and 166.2 mg of sodium chloride, and about 0.4 ml of 1 mol/L of an aqueous solution of sodium hydroxide was added with stirring to give a solution. The solution was adjusted to pH 7.0 with aqueous solution of sodium hydroxide (concentration: 1 mol/L), and diluted with water up to a total volume of 20 ml.

This solution was aseptically filtered with GV to give an eye drops formulation.

Comparative Example 3

In 14 ml of water for injection were dissolved with heating 6.6 mg of methylparaben and 3.6 mg of propylparaben. The solution was cooled down to room temperature and mixed with 0.2 g of boric acid to give a solution.

To this solution were added 0.1 g of Compound A and 61 mg of sodium chloride, and about 0.4 ml of a 1 mol/L aqueous solution of sodium hydroxide was added with stirring to give a solution. The solution was adjusted to pH 7.0 with an aqueous solution of sodium hydroxide (concentration: 1 mol/L) and mixed with water for injection up to a total volume of 20 ml.

This solution was aseptically filtered with GV to give an eye drops formulation.

Comparative Example 4

Preparation was carried out in the same manner as described in Comparative Examples 1 to 3, except that Compound B was used in place of Compound A. Thus, the following eye drops formulations a, b and c were prepared.

| Component | Formulation (mg/mL) | | |
|---|---|---|---|
| | Formulation a | Formulation b | Formulation c |
| Compound B | 20 | 20 | 20 |
| Methylparaben | 0.33 | 0.33 | 0.33 |
| Propylparaben | 0.18 | 0.18 | 0.18 |
| Boric acid | — | — | 10 |
| EDTA-2Na | — | 0.05 | — |
| Sodium chloride | 5.41 | — | 5.41 |

("EDTA-2Na" represents disodium ethylenediamine tetraacetate dihydrate. In addition to the description above, appropriate amounts of sodium hydroxide and hydrochloric acid were added for adjusting to pH 7.0.)

Experiment

The effects of the present invention are illustrated by the following experiment.

Test Example 1

Intraocular Tension Lowering Test

A model of raised intraocular tension was prepared by using New Zealand white rabbits weighing 2 to 3 kg according to the method of Kurihara et al. (Ophthalmic Pharmacology, Vol. 4, 62–64, 1990), and the intraocular tension lowering activity of the test compositions was examined. That is, rabbits were totally paralyzed with urethane, and the intraocular tension was measured with Alcon Applanation Pneumotonography.

The rabbit's eye was treated with a topical anesthetic, and 0.1 ml of a 5% aqueous solution of sodium chloride was injected into the glass body through a 30 gauge injection needle. Half an hour after the injection, elevation of intraocular tension was confirmed, and 50 μl of a test composition was dropped. (As a control, a physiological saline solution was dropped.)

After dropping, the intraocular tension was measured every 30 minutes. The lowering of intraocular tension (mmHg) was calculated from the intraocular tension of the group in which the test composition was dropped and that of the group in which the control composition was dropped.

The results are shown in Table 1-1 and Table 1-2. (Note: the formulation of each composition used for the experiment is shown in Table 2-1 and Table 2-2, respectively.)

TABLE 1-1

Intraocular Tension Lowering Activity

| Test composition | Intraocular tension lowering (mmHg) | | | | |
|---|---|---|---|---|---|
| | 0 | 30 | 60 | 90 | 120 (min) |
| Composition 1 | −0.6 ± 1.0 | −7.1 ± 2.4 | −6.9 ± 3.0 | −6.5 ± 1.8 | −1.5 ± 1.8 |
| Composition 2 | −0.9 ± 1.6 | −4.3 ± 3.2 | −1.7 ± 2.7 | −2.6 ± 3.4 | 2.0 ± 1.6 |
| Composition 3 | −0.6 ± 1.5 | −5.0 ± 2.5 | −3.8 ± 2.5 | −3.2 ± 2.5 | 0.3 ± 1.9 |
| Composition 4 | −0.5 ± 1.5 | −4.1 ± 2.5 | −1.3 ± 3.0 | −2.3 ± 2.2 | 2.0 ± 2.3 |

TABLE 1-2

Intraocular Tension Lowering Activity

| Test composition | Intraocular tension lowering (mmHg) | | | |
|---|---|---|---|---|
| | 0 | 30 | 60 | 90 (min) |
| Composition 5 | −0.3 ± 2.1 | −8.3 ± 2.3 | −11.6 ± 1.8 | −9.5 ± 2.1 |
| Composition 6 | 0.1 ± 1.6 | −5.4 ± 1.5 | −6.6 ± 2.3 | −8.0 ± 1.8 |
| Composition 7 | −0.1 ± 1.6 | −5.2 ± 1.9 | −9.0 ± 2.0 | −7.7 ± 1.3 |
| Composition 8 | −0.2 ± 1.0 | −7.1 ± 3.4 | −6.2 ± 3.0 | −7.6 ± 2.6 |

TABLE 2-1

Formulation of Each Composition (mg/mL)

| Ingredient | Composition 1 (Composition of Example 1) | Composition 2 (Composition of Comparative Example 1) | Composition 3 (Composition of Comparative Example 2) | Composition 4 (Composition of Comparative Example 3) |
|---|---|---|---|---|
| Compound A | 5 | 5 | 5 | 5 |
| MP | 0.33 | 0.33 | 0.33 | 0.33 |
| PP | 0.18 | 0.18 | 0.18 | 0.18 |
| Boric acid | 10 | — | — | 10 |
| EDTA-2Na | 0.05 | — | 0.05 | — |
| NaCl | 3.05 | 8.31 | 8.31 | 3.05 |

TABLE 2-2

Formulation of Each Composition (mg/mL)

| Ingredient | Composition 5 (Composition of Example 2) | Composition 6 (Composition of formulation a, Comparative Example 4) | Composition 7 (Composition of formulation b, Comparative Example 4) | Composition 8 (Composition of formulation c, Comparative Example 4) |
|---|---|---|---|---|
| Compound B | 20 | 20 | 20 | 20 |
| MP | 0.33 | 0.33 | 0.33 | 0.33 |
| PP | 0.18 | 0.18 | 0.18 | 0.18 |
| Boric acid | 10 | — | — | 10 |
| EDTA-2Na | 0.05 | — | 0.05 | — |
| NaCl | — | 5.41 | 5.41 | — |

(In the above tables, "MP" represents methylparaben, "PP" represents propylparaben, and "EDTA-2Na" represents disodium ethylenediamine tetraacetate dihydrate. In addition to the description above, appropriate amounts of sodium hydroxide and hydrochloric acid were added for adjusting to pH 7.0.)

It was found from the results of Compositions 2 to 4 and Compositions 6 to 8 that there was hardly an influence on the intraocular tension lowering degree when boric acids alone or ethylenediamine tetraacetic acids alone were used in combination with angiotensin II antagonists.

In contrast to these results, Composition 1 containing boric acids and ethylenediamine tetraacetic acids together showed marked intraocular tension lowering activity compared with Compositions 2 to 4. Similarly, Composition 5 showed marked intraocular tension lowering activity compared with Compositions 6 to 8. Thus, the intraocular tension lowering activity of angiotensin II antagonists was markedly increased by adding a combination of boric acids and ethylenediamine tetraacetic acids, as shown by the results of Table 1-1 and Table 2-2.

The intraocular tension lowering composition and method for topical administration of the present invention shows excellent intraocular tension lowering activity with weak side effects and can lower effectively the intraocular tension raised by glaucoma (including normal tension glaucoma) and ocular hypertension, etc.

We claim:

1. A pharmaceutical composition for topical application comprising pharmacologically active agents in amounts effective to lower intraocular tension together with a carrier therefor, wherein said pharmacologically active agents comprise component (i) which is an angiotensin II antagonist and which is a compound of the following formula (I) or a pharmacologically acceptable salt or derivative thereof:

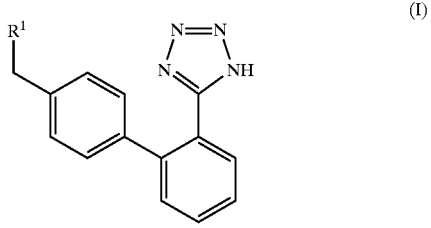

(I)

wherein $R^1$ represents a group of the following structure (Ia):

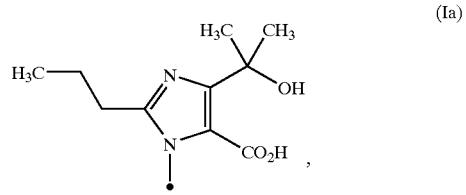

(Ia)

component (ii) which is a compound which provides a borate ion when dissolved in water and component (iii) which is a compound which provides an ethylenediamine tetraacetate ion when dissolved in water, wherein said component (i) is in an amount of from about 0.001% to 10%; said component (ii) is in an amount of from about 0.05% to 10%; and said component (iii) is in an amount of from about 0.00025% to 0.2%; all percents are by weight of the respective component in grams per 100 mL of the total volume of said composition; the percent of component (ii) is calculated based on the amount of boric acid to provide the borate ion and the percent of component (iii) is calculated based on the amount of disodium ethylenediamine tetraacetate dihydrate to provide the ethylenediamine tetraacetate ion.

2. The composition of claim 1, wherein the weight ratio of said component (iii) to said component (ii) is from 0.00025:1 to 0.2:1.

3. The composition of claim 1, wherein the derivative of said compound of formula (I) is one or more groups selected from the group consisting of esters of hydroxyl groups, ethers of hydroxyl groups, esters of carboxyl groups and amides of carboxyl groups.

4. The composition of claim 3, wherein said component (i) is in an amount of from 0.01% to 5%; said component (ii) is in an amount of from 0.1% to 5%; and said component (iii) is in an amount of from 0.0005% to 0.1%; all percents are by weight of the respective component in grams per 100 mL of the total volume of said composition; the percent of component (ii) is calculated based on the amount of boric acid to provide the borate ion and the percent of component (iii) is calculated based on the amount of disodium ethylenediamine tetraacetate dihydrate to provide the ethylenediamine tetraacetate ion; and the weight ratio of said component (iii) to said component (ii) is from 0.0005:1 to 0.1:1.

5. The composition of claim 3, wherein said component (i) is in an amount of from 0.01% to 5%; said component (ii) is in an amount of from 0.5% to 2%; and said component (iii) is in an amount of from 0.005% to 0.05%; all percents are by weight of the respective component in grams per 100 mL of the total volume of said composition; the percent of component (ii) is calculated based on the amount of boric acid to provide the borate ion and the percent of component (iii) is calculated based on the amount of disodium ethylenediamine tetraacetate dihydrate to provide the ethylenediamine tetraacetate ion; and the weight ratio of said component (iii) to said component (ii) is from 0.005:1 to 0.05:1.

6. The composition of any one of claim 2, 4 or 5, wherein said compound of the formula (I) is 4-(1-hydroxy-1-methylethyl)-2-propyl-1-{4-[2-(tetrazol-5-yl)phenyl]phenyl}-methylimidazole-5-carboxylic acid.

7. The composition of claim 6, wherein said composition further comprises a preservative.

8. The composition of claim 6, wherein said composition further comprises at least one paraben selected from methylparaben and propylparaben as a preservative.

9. The composition of claim 8, wherein said component (i) is provided as 4-(1-hydroxy-1-methylethyl)-2-propyl-1-{4-[2-(tetrazol-5-yl)phenyl]phenyl}-methylimidazole-5-carboxylic acid, said component (ii) is provided as boric acid and said component (iii) is provided as disodium ethylenediamine tetraacetate dihydrate.

10. A method of lowering intraocular tension in a human in need thereof, comprising administering to an eye of said human, an effective amount of a pharmacological composition according to claim 9.

11. A method of lowering intraocular tension in a human in need thereof, comprising administering to an eye of said human, an effective amount of a pharmacological composition according to claim 8.

12. The composition of claim 6, wherein said component (i) is provided as 4-(1-hydroxy-1-methylethyl)-2-propyl-1-{4-[2-(tetrazol-5-yl)phenyl]phenyl}-methylimidazole-5-carboxylic acid, said component (ii) is provided as boric acid and said component (iii) is provided as disodium ethylenediamine tetraacetate dihydrate.

13. A method of lowering intraocular tension in a human in need thereof, comprising administering to an eye of said human, an effective amount of a pharmacological composition according to claim 12.

14. A method of treating glaucoma or ocular hypertension in a human in need thereof comprising administering to an eye of said human, an amount of a pharmacological composition according to claim 12 effective to lower intraocular tension.

15. A method of lowering intraocular tension in a human in need thereof, comprising administering to an eye of said human, an effective amount of a pharmacological composition according to claim 6.

16. A method of treating glaucoma or ocular hypertension in a human in need thereof comprising administering to an eye of said human, an amount of a pharmacological composition according to claim 6 effective to lower intraocular tension.

17. The composition of any one of claim 1, 3 or 4, wherein said composition further comprises a preservative.

18. A method of lowering intraocular tension in a human in need thereof, comprising administering to an eye of said human, an effective amount of a pharmacological composition according to claim 17.

19. The composition of any one of claim 1, 3, 4 or 5, wherein said composition further comprises a paraben as a preservative.

20. The composition of any one of claim 1, 3, 4 or 5, wherein said component (ii) is provided as boric acid and said component (iii) is provided as disodium ethylenediamine tetraacetate dihydrate.

21. A method of lowering intraocular tension in a human in need thereof, comprising administering to an eye of said human, an effective amount of a pharmacological composition according to claim 20.

22. The composition of claim 1 which is an aqueous composition.

23. The composition of claim 1 which is a non-aqueous composition.

24. A method of lowering intraocular tension in a warm-blooded animal in need thereof, comprising administering to an eye of said warm-blooded animal, an effective amount of a pharmacological composition according to any one of claim 1, 2, 3, 4 or 5.

25. A method of treating glaucoma or ocular hypertension in a human in need thereof comprising administering to an eye of said human, an amount of a pharmacological composition according to claim 1 effective to lower intraocular tension.

26. A method of lowering intraocular tension in a human in need thereof, comprising administering to an eye of said human (i) an angiotensin II antagonist, said angiotensin II antagonist being a compound of the following formula (I) or a pharmacologically acceptable salt or derivative thereof:

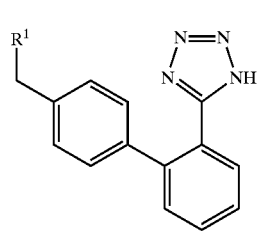

wherein $R^1$ represents a group of the following structure (Ia):

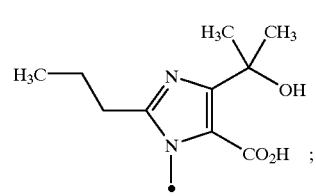

(ii) a compound which provides a borate ion when dissolved in water; and (iii) a compound which provides an ethylene diamine tetraacetate ion when dissolved in water; said angiotensin II antagonist, said compound which provides a borate ion and said compound which provides an ethylene diamine tetraacetate ion being in amounts effective to lower intraocular tension in said eye, wherein said component (i) is in an amount of from about 0.001% to 10%; said component (ii) is in an amount of from about 0.05% to 10%; and said component (iii) is in an amount of from about 0.00025% to 0.2%; all percents are by weight of the respective component in grams per 100 mL of the total volume of said composition; the percent of component (ii) is calculated based on the amount of boric acid to provide the borate ion and the percent of component (iii) is calculated based on the amount of disodium ethylenediamine tetraacetate dihydrate to provide the ethylenediamine tetraacetate ion.

27. A method according to claim 26, wherein at least two of said (i), (ii) and (iii) are administered separately, but substantially simultaneously.

* * * * *

UNITED STATES PATENT AND TRADEMARK OFFICE
CERTIFICATE OF CORRECTION

PATENT NO. : 6,777,436 B2 Page 1 of 1
APPLICATION NO. : 10/016535
DATED : August 17, 2004
INVENTOR(S) : Tomihisa Yokoyama et al.

It is certified that error appears in the above-identified patent and that said Letters Patent is hereby corrected as shown below:

Column 16, lines 30 to 33 (Claim 6) : Cancel in its entirety .

Column 16, lines 34, 36 and 53 (in line 1 of each of Claims 7, 8 and 12) , replace "6" with --2, 4 or 5-- .

Column 17, lines 4 and 8 (in line 4 of each of Claims 15 and 16) , replace "6" with --2, 4 or 5-- .

Signed and Sealed this

Second Day of October, 2007

JON W. DUDAS
*Director of the United States Patent and Trademark Office*